US010798963B2

(12) United States Patent
Maynard et al.

(10) Patent No.: US 10,798,963 B2
(45) Date of Patent: Oct. 13, 2020

(54) MILK-BASED PROTEIN HYDROLYSATES AND COMPOSITIONS MADE THEREOF

(71) Applicant: NESTEC S.A., Vevey (CH)

(72) Inventors: Francoise Maynard, La Conversion (CH); Delphine Salvatore, Biglen (CH); Anne Thevenier, Bern (CH)

(73) Assignee: Societe des Produits Nestle S.A., Vevey (CH)

(*) Notice: Subject to any disclaimer, the term of this patent is extended or adjusted under 35 U.S.C. 154(b) by 0 days.

(21) Appl. No.: 15/560,549

(22) PCT Filed: Mar. 21, 2016

(86) PCT No.: PCT/EP2016/056080
§ 371 (c)(1),
(2) Date: Sep. 22, 2017

(87) PCT Pub. No.: WO2016/156077
PCT Pub. Date: Oct. 6, 2016

(65) Prior Publication Data
US 2018/0116270 A1    May 3, 2018

(30) Foreign Application Priority Data
Mar. 30, 2015  (EP) .................................. 15161655

(51) Int. Cl.
| | |
|---|---|
| A23L 3/34 | (2006.01) |
| A23C 21/02 | (2006.01) |
| C12N 9/56 | (2006.01) |
| C12N 9/62 | (2006.01) |
| C12N 9/50 | (2006.01) |
| C12N 9/48 | (2006.01) |
| A23L 33/00 | (2016.01) |
| A23L 29/00 | (2016.01) |
| A23L 33/18 | (2016.01) |
| A23L 33/19 | (2016.01) |
| C12N 9/54 | (2006.01) |
| A23J 3/34 | (2006.01) |

(52) U.S. Cl.
CPC .............. *A23L 33/40* (2016.08); *A23C 21/02* (2013.01); *A23J 3/343* (2013.01); *A23J 3/344* (2013.01); *A23L 29/06* (2016.08); *A23L 33/18* (2016.08); *A23L 33/19* (2016.08); *C12N 9/54* (2013.01); *C12N 9/62* (2013.01); *C12N 9/63* (2013.01); *A23V 2002/00* (2013.01); *A23V 2200/266* (2013.01); *A23V 2250/5424* (2013.01)

(58) Field of Classification Search
None
See application file for complete search history.

(56) References Cited

U.S. PATENT DOCUMENTS

| | | | | |
|---|---|---|---|---|
| 4,100,024 A | * | 7/1978 | Adler-Nissen | A23J 3/346 435/68.1 |
| 5,952,193 A | * | 9/1999 | Shimamura | A61K 38/01 435/68.1 |
| 2002/0192333 A1 | | 12/2002 | Christensen et al. | |
| 2010/0233318 A1 | * | 9/2010 | Edens | A23C 9/1209 426/41 |

FOREIGN PATENT DOCUMENTS

| | | |
|---|---|---|
| EP | 0226221 | 6/1987 |
| JP | 2002354980 | 12/2002 |
| WO | 9613174 | 5/1996 |
| WO | 2004069265 | 8/2004 |
| WO | 2014130007 | 8/2014 |
| WO | 2015039135 | 3/2015 |

OTHER PUBLICATIONS

Johnston, Infant formulas explained, S. Afr. Fam. Pract., 2011, 53, 433-36.*
Doucet et al., Enzyme-Induced Gelation of Extensively Hydrolyzed Whey Proteins by Alcalase, J. Agric. Food Chem., 2003, 51, 6300-07.*
Smirnova et al., A New Enzyme Preparation with High Penicillopepsin Activity Based on the Producer Strain Penicillium canescens, Appl. Biochem. Microbiol., 2015, 51, 660-66.*
Merz et al., Flavourzyme, an Enzyme Preparation with Industrial Relevance: Automated Nine-Step Purification and Partial Characterization of Eight Enzymes, J. Agric. Food Chem., 2015, 63, 5682-93.*
Nakamura et al. "Enzymatic production of hypoallergenic peptides from casein" Milchwissenschaft, 1993, vol. 48, No. 1, pp. 11-14.

* cited by examiner

*Primary Examiner* — Robert B Mondesi
*Assistant Examiner* — Todd M Epstein
(74) *Attorney, Agent, or Firm* — K&L Gates LLP

(57) ABSTRACT

A process for preparing a milk protein hydrolysate comprising hydrolysing a milk-based proteinaceous material with a microbial alkaline serine protease in combination with bromelain, a protease from *Aspergillus* and a protease from *Bacillus*.

7 Claims, 1 Drawing Sheet

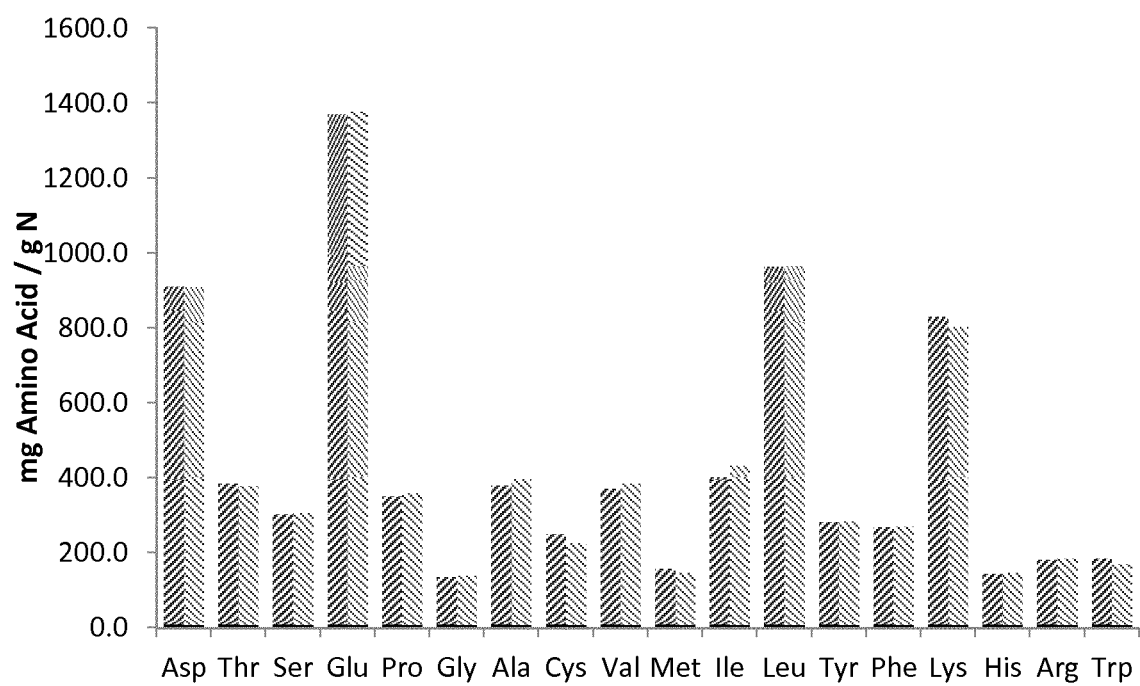

MILK-BASED PROTEIN HYDROLYSATES AND COMPOSITIONS MADE THEREOF

CROSS REFERENCE TO RELATED APPLICATIONS

The present application is a National Stage of International Application No. PCT/EP2016/056080, filed on Mar. 21, 2016, which claims priority to European Patent Application No. 15161655.4, filed on Mar. 30, 2015, the entire contents of which are being incorporated herein by reference.

FIELD OF INVENTION

The present invention relates to compositions comprising a milk-based protein hydrolysate using enzymes from microbial origin and plant origin. The compositions may be incorporated into infant formulas and food supplements.

The present invention avoids the use of porcine-derived enzymes thereby providing compositions with Halal status.

BACKGROUND

Human breast milk and breast feeding represent the uncontested gold standard in terms of infant nutrition. Infant formulae that serve as a substitute for or complement to human breast milk should satisfy the nutritional requirements of infants, have an acceptable taste and be hypoallergenic when targeted to infants at risk of allergy and/or food intolerances.

It is known that allergies to cows' milk and to infant formulae containing cows' milk protein are due to the fact that the proteins of cows' milk differ from the proteins of mother's milk and can constitute allergens for humans. The principal recognized cows' milk allergens are alpha-lactalbumin (aLA), beta-lactolglobulin (bLG) and bovine serum albumin (BSA).

Bovine whey proteins and/or caseins are often used as the milk proteins source in infant formulae.

To reduce allergenicity, cows' milk proteins are hydrolysed by enzymes and thus reduced to peptides. The hydrolysis process used to produce these hydrolysates must be carefully monitored so that the final product retains its nutritional value and desired physical properties but is hypoallergenic.

Hydrolysates may be characterised as "partial" or "extensive" depending on the extent to which the hydrolysis reaction is carried out. Currently there is no agreed legal/clinical definition of Extensively Hydrolyzed Products (EHP) according to the WAO (World Allergy Organization) guidelines for cows' milk protein allergy (CMA) but there is agreement that hydrolyzed formulas have proven to be a useful and widely used protein source for infants suffering from Cow Milk Allergies (CMA). An extensive hydrolysate may be defined as one in which at least 95% of the protein/peptide population has a molecular weight of less than 1000 Daltons whereas a partial hydrolysate may be defined as one in which 60% of the protein/peptide population has a molecular weight of less than 1000 Daltons. These definitions are currently used in the industry.

It has been stressed by both the European Society for Paediatric Allergy and Clinical Immunology (ESPACI) and the European Society for Paediatric Gastroenterology, Hepatology, and Nutrition (ESPGHAN) that extensively hydrolysed formulae should be used in IgE mediated CMA owing to their proven safety and hypoallergenicity (Businco et al. *Pediatr Allergy Immunol* 1993, 4:101-111; Host et al. *Arch Dis Child* 1999, 81:80-84; American Academy of Pediatrics, *Pediatrics* 1989, 83:1068-1069).

Many groups have carried out research in order to optimise the hydrolysis process. Hydrolysis reaction conditions including temperature and reactor volume, number of cycles of hydrolysis, choice of protein substrate, enzyme(s) type and concentration are some of the many factors that influence the hydrolysis reaction and thus the physical, chemical and ultimately biological properties of the final product.

Porcine enzymes, in particular porcine pancreatic enzymes are commonly used in the hydrolysis process. For example, in EP0353122, mixtures of trypsin and chymotrypsin at specific ratios are used to prepare hypoallergenic whey protein hydrolysates. WO9304593 A1 and U.S. Pat. No. 5,039,532A also disclose a hydrolysis process using trypsin and chymotrypsin, which includes a two-step hydrolysis reaction with a heat denaturation step in between to ensure that the final hydrolysate is substantially free of intact allergenic proteins. The trypsin and chymotrypsin used in these methods are preparations produced by extraction of porcine pancreas.

A number of products containing protein hydrolysates prepared using animal enzymes exist on the market. For example, a Nestle HA® infant formula may be prepared with a hydrolysate produced using trypsin and chymotrypsin extracted from animal pancreas. Furthermore, the extensively hydrolysed products Alfaré® and Althéra® may also be prepared using porcine pancreatin.

There is a need in the art for products containing protein hydrolysates prepared using non-porcine enzymes. Advantageously, such products may have Halal status. However, non-porcine enzyme-based hydrolysates should have peptidic profiles that substantially correspond to hydrolysates obtained from porcine enzyme and should maintain the hypoallergenic properties. Whilst this represents a considerable challenge it is particularly important since any new infant formula on the market is submitted to strict regulatory guidelines, for example in Europe Directive 2006/141/EC applies.

The present invention addresses the need for products containing protein hydrolysates prepared using non-porcine enzymes.

SUMMARY OF THE INVENTION

The inventors have carried out an extensive research programme, in an attempt to identify non-porcine enzymes as potential candidates for carrying out the hydrolysis reaction. In particular, the inventors have identified enzyme combinations that may replace the porcine enzymes used in the preparation of marketed hydrolysed products, in particular Alfaré® and Althéra®.

The inventors have monitored parameters including hydrolysis reaction performance and peptide molecular weight profile and have determined enzyme mixtures that provide hydrolysates with the desired physical, chemical and biological properties.

The milk protein hydrolysates disclosed herein may be produced efficiently and reproducibly, have the required nutritional value and are hypoallergenic.

According to a first aspect of the present invention there is provided a process for preparing a milk protein hydrolysate comprising hydrolysing a milk-based proteinaceous material with a microbial alkaline serine protease, bromelain, a protease from *Aspergillus* and a protease from *Bacillus*.

Preferably the process comprises hydrolysing a milk-based proteinaceous material with a microbial alkaline serine protease, bromelain, two proteases from *Aspergillus* and a protease from *Bacillus*.

Preferably the microbial alkaline serine protease is a subtilisin, preferably a subtilisin Carlsberg.

In one embodiment the alkaline serine protease is derived from *Bacillus*, preferably *Bacillus licheniformis*. An example of an alkaline serine protease for use in the invention is Alcalase™.

Preferably the two proteases from *Aspergillus* are a leucine aminopeptidase and aspergillopepsin 1.

Preferably the proteases from *Aspergillus* are from *Aspergillus oryzae*.

Preferably the protease form *Bacillus* is from *Bacillus subtilis*.

Preferably the protease from *Bacillus* is *Bacillus subtilis* neutral proteinase.

Preferably the process comprises:
(i) a first hydrolysis step comprising hydrolysing the milk-based proteinaceous material with the microbial alkaline serine protease; and
(ii) a second hydrolysis step comprising hydrolysing the milk protein with bromelain in combination with the *Aspergillus* and *Bacillus* proteases.

The milk-based proteinaceous material may be, for example, whey protein, casein or mixtures of both. Preferably the milk-based proteinaceous material is whey protein.

Preferably the hydrolysate is further subjected to enzyme inactivation, microfiltration and ultrafiltration.

In a particularly preferred embodiment the protein hydrolysate is an extensively hydrolysed product wherein the extent of hydrolysis (Non Protein Nitrogen/Total Nitrogen ratio, NPN/TN %) is greater than 95%, preferably greater than 99%.

The present invention is particularly useful in providing "extensive" protein hydrolysates present in formulae such as those intended to feed cows' milk allergic infants and children. Such hydrolysates are preferably directed to sick (allergic) infants and children that are already sensitized to cows' milk proteins.

Thus, according to another aspect of the present invention there is provided a composition comprising a milk-based protein hydrolysate obtained by the process of the invention. The composition may be, for example, an infant formula, follow-on formula, a baby food formula, a child's food supplement or an adult nutritional composition.

In a preferred embodiment the composition is an infant formula, preferably a hypoallergenic infant formula.

The present invention also provides protein hydrolysates, compositions and methods of producing the same useful in infant, child, or adult products targeting other benefits than those related to allergy, such as: facilitated digestion; enhanced absorption and metabolisation of amino-acids, peptides and proteins; promoted recovery from sickness; and optimized utilization of nitrogen sources.

According to another aspect of the present invention there is provided use of bromelain in the preparation of a composition comprising a hydrolysate of a milk-based proteinaceous material.

Preferably the use of bromelain is in conjunction with the use of the microbial alkaline serine protease and proteases from *Aspergillus* and *Bacillus* species referred to herein.

According to another aspect of the present invention there is provided use of a milk protein hydrolysate obtained according to the process of the invention in the preparation of an infant formula.

According to another aspect of the present invention there is provided a composition defined herein for use in reducing or preventing food intolerance, cows' milk protein allergy (CMA), chronic diarrhoea and malabsorption.

According to another aspect of the present invention there is provided use of the composition as defined herein for reducing or preventing food intolerance, cows' milk protein allergy (CMA), chronic diarrhoea and malabsorption.

According to another aspect of the present invention there is provided a method of administering a composition of the present invention to a subject wherein the subject has food intolerance, cows' milk protein allergy (CMA), chronic diarrhoea and malabsorption.

DESCRIPTION OF THE FIGURES

FIG. 1: Shows the amino acid profiles of UF permeate using the enzyme combinations according to the invention, determined in two different trials (left-hand bar $1^{st}$ trial, right-hand bar $2^{nd}$ trial).

DETAILED DESCRIPTION OF THE INVENTION

The milk-based protein hydrolysate of the present invention is obtained by the treatment of a solution of a milk-based proteinaceous material with the proteases referred to herein.

Milk-Based Proteinaceous Material

The milk-based protein hydrolysate is preferably a milk-based proteinaceous material. It may be a whey-based proteinaceous material, casein or mixtures of whey-based proteinaceous material and casein.

The casein source may be acid casein or non-fat milk solids.

Preferably the milk-based proteinaceous material is whey based.

The whey based proteinaceous material may be a whey from cheese making, particularly a sweet whey such as that resulting from the coagulation of casein by rennet, an acidic whey from the coagulation of casein by an acid, or the acidifying ferments, or even a mixed whey resulting from coagulation by an acid and by rennet. This starting material may be whey that has been demineralized by ion exchange and/or by electrodialysis and is known as demineralised whey protein (DWP).

The source of such whey-based proteinaceous material may be sweet whey from which the caseino-glycomacropeptide (CGMP) has been totally or partially removed. This is called modified sweet whey (MSW). Removal of the CGMP from sweet whey results in a protein material with threonine and trytophan contents that are closer to those of human milk. A process for removing CGMP from sweet whey is described in EP 880902. The starting material may be a mix of DWP and MSW. It may be a concentrate wherein the whey protein is 35-80% protein (WPC) or an isolate if the whey protein concentration is more than 95% protein (WPI). An example of WPC is WPC 87 Lacprodan® available from Aria Foods, Denmark and an example of WPI is Bipro® from Davisco Foods International (Minnesota USA).

Preferably the milk-based proteinaceous material is whey protein isolate (WPI).

The milk based proteinaceous material may be in solution or suspension, and may be, for example, present at a concentration of 2-30% by weight of proteinaceous material, more preferably 5-20%, more preferably 6-10%. In one embodiment the milk based proteinaceous material is present at a concentration of about 6%.

Addition of lactose to starting material for hydrolysis has the advantage that any residual protein contained in the lactose is hydrolysed. Lactose may be present in concentrations from 0.05-30% w/w, preferably 0.10-20% w/w, or in cases where a lower lactose content is preferred, 0.10 to 1%, preferably 0.10 to 0.20% (w/w). In the latter case the final product may be destined for subjects with a low lactose tolerance. Lactose may be removed, for example, by ultrafiltration (yielding UF whey), optionally followed by dialysis. In one embodiment the lactose is present at a concentration of about 2%.

The starting material may be in the form of a true or colloidal aqueous solution, or in the form of a powder. In the latter case, the powder is dissolved in preferably demineralised water to form an aqueous solution Enzymes Used in Hydrolysis
Microbial Alkaline Serine Protease The microbial alkaline serine protease is preferably derived from a *Bacillus* species, more preferably from *Bacillus licheniformis*.

In a preferred embodiment the alkaline serine protease is a subtilisin.

Examples of subtilisins are those derived from *Bacillus*, e.g., subtilisin Novo, subtilisin Carlsberg, subtilisin BPN' subtilisin 309, subtilisin 147 and subtilisin 168 (described in WO 89/06279) and Protease PD138 (WO 93/18140). Examples are described in WO 98/020115, WO 01/44452, WO 01/58275, WO 01/58276, WO 03/006602 and WO 04/099401.

An example of an alkaline serine protease is subtilisin Carlsberg enzyme Uniprot P00780 or a variant thereof.

In a particularly preferred embodiment the alkaline serine protease for use in the invention is Alcalase™.

Bromelain

The term 'bromelain' is well known in the art. Bromelain may be referred to as an extract derived from members of the Bromeliaceae family which comprises various thiol proteases and is known to have proteolytic activity in vitro and in vivo.

Preferably the extract is derived from the stem of *Ananas comosus* (pineapple). The extract may include elements such as cysteine proteases, amylase, acid phosphatase, peroxidases and cellulases.

The enzyme may have the following EC Number: EC 3.4.22.32.

Bromelain may comprise the: 'stem bromelain' (UniProt P14518) or a variant thereof.

*Aspergillus* Proteases
Leucine Amino Peptidase

Preferably an *Aspergillus* leucine amino peptidase is used in the present invention. More preferably, an *Aspergillus oryzae* leucine amino peptidase is used in the present invention.

The enzyme may have the following EC Number: EC 3.4.11.1.

A leucine amino peptidase preferably catalyses the hydrolysis of residues at the N-terminus of peptides, preferably the hydrolysis of leucine residues.

Examples of leucine amino peptidase enzymes which are expressed by *Aspergillus oryzae* include LAPA (UniProt Q2U1F3), LAP1 (UniProt Q2PIT3) and LAP2 (UniProt Q2ULM2)).

Aspergillopepsin 1

Preferably Aspergillopepsin 1 derived from *Aspergillus* species is used in the present invention. More preferably *Aspergillus oryzae* Aspergillopepsin 1 is used in the present invention. Other names for Aspergillopepsin 1 commonly used in the art include, inter alia, Aspergillopepsin A, Aspergillopepsin F and Aspergillopeptidase A.

The enzyme may have the following EC Number: EC 3.4.23.18.

Aspergillopepsin 1 enzymes preferably catalyse the hydrolysis of polypeptides with a broad specificity, preferably the hydrolysis of peptide bonds between hydrophobic residues.

*Bacillus* Protease

A protease from *Bacillus* species is preferably used in the process of the present invention. Preferably *Bacillus subtilis* neutral proteinase is used in the process of the present invention. Other names for *Bacillus subtilis* neutral proteinase commonly used in the art include, inter alia, bacillolysin, *Bacillus* metalloendopeptidase, megateriopeptidase, *Bacillus* neutral protease and *Bacillus* extracellular neutral metalloprotease.

Preferably the *Bacillus subtilis* neutral proteinase is from *Bacillus subtilis*.

The *Bacillus* protease may have the following EC Number: 3.4.24.28.

An example of a *Bacillus* protease is NPRE (UniProt P68763) or a variant thereof.

The Hydrolysis Process

The typical conditions for carrying out the hydrolysis process have been described in the prior art. The temperature may range from about 40° C. to 60° C., for example about 55° C. The reaction time may be, for example, from 1 to 10 hours and pH values before starting hydrolysis may, for example, fall within the range 6.5 to 8.5, preferably 7.0 to 8.0.

The pH may be adjusted with known agents, for example $Ca(OH)_2$.

In one embodiment, the process comprises:
(i) a first hydrolysis step comprising hydrolysing the milk-based proteinaceous material with the microbial alkaline serine protease; and
(ii) a second hydrolysis step comprising hydrolysing the milk protein with bromelain in combination with the proteases from *Aspergillus* and the protease from *Bacillus*.

Step (i) may be performed, for example, for about four hours and step (ii) may be performed, for example, for about six hours.

Irrespective of how the hydrolysis is carried out, the hydrolysis product undergoes a heat treatment, which inactivates the enzyme carrying out the hydrolysis. This heat treatment preferably comprises preheating the hydrolysate to a temperature of or above 75° C. (for example 75° C. to 90° C.) and keeping it at that temperature for about 0.1 to 30 minutes to promote auto-digestion of the enzyme. This treatment may be followed by sterilization, preferably at ultra-high temperature, for example at 125° C.-135° C. for 30 seconds to 3 minutes by injection of steam or in a heat exchanger.

The hydrolysate thus obtained may be clarified, microfiltered and/or ultrafiltrated to remove residual protein large fragments. It may also be concentrated, for example by reverse osmosis. It may then be dried, for example by lyophylisation, spray drying, or by freeze drying for different applications, or may even be subsequently treated. In the latter case, the enzyme may be inactivated during the subsequent treatment.

The hydrolysates of the invention may have an extent of hydrolysis that is characterised by NPN/TN % content.

NPN/TN % ratio means the Non Protein Nitrogen divided by the Total Nitrogen×100. The non-protein Nitrogen is the nitrogen fraction obtained after acid precipitation of proteins. NPN/TN % may be measured as detailed in Adler-Nissen J-, 1979, J. Agric. Food Chem., 27 (6), 1256-1262.

Alternatively, the extent of hydrolysis may be characterized by the amount of amino nitrogen released upon hydrolysis; free amino nitrogen can react with a reagent such as trinitrobenzenesulfonic acid (TNBS).

In general, extensive hydrolysates are characterised as having a NPN/TN % of greater than 95%, whereas partially hydrolysed hydrolysates are characterized as having a NPN/TN % in the range 75%-85%. In a preferred embodiment the hydrolysates of the invention are extensive hydrolysates having an NPN/TN % in the range of greater than 95%, 96%, 97%, 98% or 99%.

These hydrolysates may also be characterised in that at least 95% their protein/peptide population has a molecular weight of <1000 Daltons.

The molecular weight distribution of the peptides in the protein hydrolysate obtained may be determined, e.g., by size exclusion chromatography (SEC). In a preferred embodiment the hydrolysate of the invention has a peptide weight distribution similar or substantially identical to that of Alfaré®. Preferably the hydrolysate of the invention has a peptide weight distribution similar to or substantially identical to that of a hydrolysate made with porcine pancreatin in place of the bromelain and Aspergillus and Bacillus proteases (in particular, in place of bromelain, a leucine aminopeptidase from Apergillus oryzae, Aspergillopepsin 1 from Apergillus oryzae and Bacillus subtilis neutral proteinase) referred to herein. Put another way, the bromelain and Aspergillus and Bacillus protease blend performs substantially the same hydrolytic activity in the context of the present invention as porcine pancreatin.

In a preferred embodiment, the hydrolysate of the invention is an extensive hydrolysate and is comprised of peptides having a median molecular weight of 300 Da to 370 Da, preferably 320 Da to 360 Da.

The residual antigenicity of the hydrolysates may be evaluated using standard immunoassays such ELISA tests. Preferably the hydrolysates of the invention present a residual β-lactoglobulin (BLG) of <0.1 mg BLG equivalent/g protein equivalent, and most preferably <0.01 mg BLG equivalent/g protein.

The hydrolysates of the invention may be incorporated into infant formula, follow-on formula, a baby food, infant cereals, growing-up milk, infant or child's food supplement or an adult nutritional composition, i.e. all preparations treatment of allergy, as well as any other benefits that protein hydrolysates could provide to humans. Preferably, the hydrolysates are used in starter infant formula.

Current hypoallergenic formulas composed of such cows' milk proteins hydrolysates aimed at allergy prevention also comprise other nutrients such as animal oils, vegetable oils, starch, maltodextrin, lactose and sucrose.

In one embodiment of the invention, the hydrolysates of the invention are used in combination with selected probiotics, for example in infant formula. The selected probiotics can be any of the probiotics conventionally used in infant formula. Preferably the probiotics are those able to provide additional or synergistic effect on allergies.

Examples of suitable probiotic micro-organisms which may be used in the present invention include yeasts such as *Saccharomyces, Debaromyces, Candida, Pichia* and *Torulopsis*, moulds such as *Aspergillus, Rhizopus, Mucor*, and *Penicillium* and *Torulopsis* and bacteria such as the genera *Bifidobacterium, Bacteroides, Clostridium, Fusobacteum, Melissococcus, Propionibacteum, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei* Shirota, *Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus* {*Lactobacillus* GG}, *Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus*, and *Staphylococcus xylosus*.

Preferred probiotic bacterial strains include *Lactobacillus rhamnosus* ATCC 53103 obtainable from Valio Oy of Finland under the trade mark LGG, *Lactobacillus rhamnosus* CGMCC 1.3724, *Lactobacillus paracasei* CNCM 1-2116, *Bifidobacterium lactis* CNCM 1-3446 sold inter alia by the Christian Hansen company of Denmark under the trade mark Bb 12 and *Bifidobacterium longum* ATCC BAA-999 sold by Morinaga Milk Industry Co. Ltd. of Japan under the trade mark BB536.

The probiotics may, for example, be present in an amount of $10^3$ to $10^{12}$ cfu/g, more preferably $10^6$ to $10^{11}$ cfu/g, even more preferably $10^4$ to $10^9$ cfu/g, most preferably $10^7$ to $10^9$ cfu/g composition or per mL of composition.

Those skilled in the art will understand that they can freely combine all features of the present invention described herein, without departing from the scope of the invention as disclosed.

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology*, John Wiley & Sons, New York, N.Y. Each of these general texts is herein incorporated by reference.

EXAMPLES

Renovate Alfaré® and Althéra® are extensively hydrolysed infant formulas intended for babies with food allergies and intolerances.

Alfaré & Althéra make use of pig pancreatin preparation during manufacturing process.

A preblend of plant and microbial proteases has unexpectedly been identified as a suitable alternative to replace pancreatin in EHP productions while maintaining the biological & physiological properties of hydrolysed products, particularly Extensively Hydrolysed Products (EHP). In particular, the use of a combination of bromelain, a microbial alkaline serine protease, proteases from *Aspergillus* and a protease from *Bacillus* has been identified as a suitable alternative to pancreatin.

The present inventors have established a process for preparing a milk protein hydrolysate comprising hydrolysing a milk-based proteinaceous material with the aforementioned agents.

Example 1—Methods 500 kg Bipro (whey isolate) was hydrolysed with Alcalase®, bromelain, leucine aminopeptidase from *Apergillus oryzae*, aspergillopepsin 1 from *Apergillus oryzae* and *Bacillus subtilis* neautral proteinase from *Bacillus subtilis*.

Enzyme inactivation was achieved by heat treatment (90° C. for 5 minutes) and all residual intact proteins and large peptides were removed by micro filtration and ultrafiltration.

Example 2—Extent of Hydrolysis

NPN/TN %

The extent of hydrolysis was determined using the ratio between Non Protein Nitrogen and Total Nitrogen (NPN/TN %). Non Protein Nitrogen fraction is obtained by acid precipitation of proteins. Upon protein hydrolysis, resulting peptides will fall into the "Non Protein Nitrogen" part. Thus, NPN/TN content is increasing with increasing hydrolysis extent. The target is NPN/TN>=95% in the hydrolysate and NPN/TN>=99% after filtration.

SDS-PAGE

The extent of hydrolysis was also determined by SDS-PAGE electrophoresis using Phastsystem and silver staining, to identify any residual intact protein and large peptides (above 10 kDa) in the hydrolysate and after filtration. The total protein and peptides present in the sample are separated using a polyacrylamide gel after denaturation (treatment with SDS and heat), reduction (treatment with DTT to reduce disulfide bridges) and acylation (addition of iodoactamide to block thiols groups) of the sample. Although some intact protein and large peptides may still be present after hydrolysis, no band related to residual protein and large peptide are detected after filtration by loading on the gel a sample solution containing 2 µg Nitrogen/µL solution.

BLG-ELISA

The absence of residual antigenicity was assessed through determination of beta-lactoglobulin antigenicity using a commercially available enzyme-linked immunosorbent assay (ELISA) kit specific to beta-lactoglobulin form r-Biopharm. The target is below the limit of detection of this kit in a whey based hydrolysate, i.e. 0.01 mg beta-lactoglobulin equivalent/g protein.

Peptide Profile

Peptides generated though hydrolysis and present in the final product after filtration were characterized based on their molecular weight using size-exclusion chromatography (SE-HPLC). Molecular weight distribution (and Median value) of soluble peptides was obtained after sample dissolution in 0.1% TFA in water and using Superdex Peptide 10/300 GL Size-Exclusion column with 0.1% v/v TFA, 30% v/v ACN in water as mobile phase. Molecular weight distribution of peptides was determined in following ranges: peptides>2400 Da, 1200-2400 Da, 600-1200 Da, 240-600 Da and <240 Da. Median value is the molecular weight at which 50% of the peptides have molecular weight above this value.

Free AA/Total AA %

The release of free amino acids upon hydrolysis was determined using the ratio between free amino acid and total amino acids (free AA/Total AA %). Free amino acids content is obtained by separation of the free amino groups present in an aqueous sample extract by ion exchange chromatography (IEC) and photometric detection after post-column derivatization with ninhydrin reagent. Total amino acids content is obtained by hydrolysis of the test portion in 6 mol/L hydrochloric acid (HCl) under nitrogen (a peroxidation of cystine to cysteic acid and methionine to methionine-sulfone is applied before hydrolysis to quantify the acid stable amino acids) and separation of individual amino acids by ion-exchange chromatography as described above.

The results of three experiments using the enzyme blend of the present invention are shown in Table 1.

TABLE 1

| Combination | Targets | NPN/TN >95% | SDS Page No residual band | Peptide profile MED (50%) Da 350 | Free AA/Total AA max 25% | Residual BLG mg eq./g prot (Elisa) <0.01 mg/g |
|---|---|---|---|---|---|---|
| Alcalase; Bromelain; leucine aminopeptidase and Aspergillopepsin 1 from *Apergillus oryzae*; *Bacillus subtilis* neutral proteinase from *Bacillus subtilis* | UF permeate | 99.3 | OK | 352.8 | 10.8 | n.q. |
| As above | UF permeate | 100.0 | OK | 354.0 | 11.4 | n.q |
| As above | UF permeate | 100.5 | OK | 354.9 | 11.6 | n.q |

All results were within the target values.

The invention claimed is:

1. A process for preparing a milk protein hydrolysate, the process comprising hydrolyzing a milk-based proteinaceous material with subtilisin Carlsberg, bromelain, leucine aminopeptidase from *Apergillus oryzae*, aspergillopepsin 1 from *Apergillus oryzae*, and neutral proteinase from *Bacillus subtilis*.

2. The process according to claim 1 comprising:
    a first hydrolysis step comprising hydrolysing the milk-based proteinaceous material with subtilisin Carlsberg; and
    a second hydrolysis step comprising hydrolysing the milk protein with the bromelain, the leucine aminopeptidase, the Aspergillopepsin 1 and the neutral proteinase from *Bacillus subtilis*.

3. The process according to claim 1, wherein the milk-based proteinaceous material is selected from the group consisting of whey protein, casein and mixtures thereof.

4. The process according to claim 1, wherein the milk-based proteinaceous material is whey protein.

5. The process according to claim 1 further comprising subjecting the hydrolyzed milk-based proteinaceous material to a process selected from the group consisting of enzyme inactivation, microfiltration and ultrafiltration.

6. The process according to claim 1, wherein the milk protein hydrolysate is an extensively hydrolyzed product, and the extent of hydrolysis (NPN/TN %) is greater than 95%.

7. The process according to claim 1, wherein the extent of hydrolysis (NPN/TN %) is greater than 99%.

\* \* \* \* \*